US012382926B2

(12) United States Patent
de Gelder et al.

(10) Patent No.: US 12,382,926 B2
(45) Date of Patent: Aug. 12, 2025

(54) HIGH-SPEED DOSING

(71) Applicant: Bühler Insect Technology Solutions AG, Uzwil (CH)

(72) Inventors: Vincent de Gelder, Gorinchem (NL); Maurits Petrus Maria Jansen, Bavel (NL)

(73) Assignee: Bühler Insect Technology Solutions AG, Uzwil (CH)

( * ) Notice: Subject to any disclaimer, the term of this patent is extended or adjusted under 35 U.S.C. 154(b) by 189 days.

(21) Appl. No.: 18/043,221

(22) PCT Filed: Aug. 20, 2021

(86) PCT No.: PCT/EP2021/025317
§ 371 (c)(1),
(2) Date: Feb. 27, 2023

(87) PCT Pub. No.: WO2022/048792
PCT Pub. Date: Mar. 10, 2022

(65) Prior Publication Data
US 2024/0008448 A1 Jan. 11, 2024

(30) Foreign Application Priority Data
Sep. 2, 2020 (EP) .................................... 20194178

(51) Int. Cl.
*A01K 5/02* (2006.01)
(52) U.S. Cl.
CPC .................. *A01K 5/0283* (2013.01)
(58) Field of Classification Search
CPC ...... A01K 5/0225; A01K 39/012; A01K 5/02; A01K 5/0283
See application file for complete search history.

(56) References Cited

U.S. PATENT DOCUMENTS

| 4,129,189 A | 12/1978 | Maglecic et al. |
| 4,554,888 A * | 11/1985 | Gross ................. A01K 5/02 119/53 |
| 4,749,008 A * | 6/1988 | Whitney ............... B65B 3/28 141/83 |
| 11,627,724 B2 * | 4/2023 | Horton ................. A01K 1/10 119/51.02 |

(Continued)

FOREIGN PATENT DOCUMENTS

| CN | 108308126 A | 7/2018 |
| CN | 109258502 A | 1/2019 |

(Continued)

OTHER PUBLICATIONS

Translation of patent CN 109 258 502 A (Year: 2019).*

*Primary Examiner* — Yvonne R Abbott-Lewis
(74) *Attorney, Agent, or Firm* — Colson Law Group, PLLC

(57) ABSTRACT

In particular, particular, the present disclosure relates to a method for supplying feed for rearing insect larvae, the method comprising the steps of (o) supplying feed to a container using a coarse feed supplying means, (i) determining at a determining means the amount of feed in the container, (ii) calculating the amount of feed necessary to bring the total amount of feed in the container to a predetermined amount of feed, and (iii) supplying feed to the container in the amount calculated in step (ii) using a fine feed supplying means.

19 Claims, 3 Drawing Sheets

(56) References Cited

U.S. PATENT DOCUMENTS

| | | | | |
|---|---|---|---|---|
| 11,707,052 | B2* | 7/2023 | Candelier | A01K 5/0283 |
| | | | | 119/51.02 |
| 2013/0092087 | A1* | 4/2013 | Bachman | B01F 35/881 |
| | | | | 119/51.01 |
| 2015/0272083 | A1* | 10/2015 | Büyükkutlu | A01K 5/0275 |
| | | | | 119/57.92 |
| 2017/0360014 | A1 | 12/2017 | Hall et al. | |
| 2020/0260699 | A1 | 8/2020 | Massaro et al. | |
| 2023/0210097 | A1* | 7/2023 | Massaro | G06Q 50/02 |
| | | | | 119/6.6 |
| 2023/0309509 | A1* | 10/2023 | Gopinath | A01K 27/009 |
| | | | | 119/51.02 |

FOREIGN PATENT DOCUMENTS

| | | |
|---|---|---|
| DE | 19855377 A1 | 6/2000 |
| EP | 0288415 A2 | 10/1988 |
| EP | 0680879 A1 | 11/1995 |
| EP | 2986107 B1 | 10/2017 |

\* cited by examiner

HIGH-SPEED DOSING

The present invention provides a method and system for providing feed for rearing insect larvae.

At the beginning of and during rearing and growth of insect larvae, feed must be supplied in correct quantity in order to ensure an optimum and healthy growth of the insects. Correct dosing of the amount of feed and velocity of the process are important factors for efficient managing of rearing of insects.

EP 2 986 107 B1 for example discloses a method and system for breeding insects including an observation station to obtain the weight of an individual crate including its substrate and insect content as well as a feed station to add additional feedstock.

Other systems largely rely on manual labour and thus show deficiencies with respect to speed, accuracy and efficiency.

However, there is a need for accurate and high-speed dosing in the field of rearing insects. This object is achieved with the features of the independent claims; the dependent claims define embodiments of the present invention.

In particular, the present disclosure relates to a method for supplying feed for rearing insect larvae, the method comprising the steps of
(o) supplying feed to a container using a coarse feed supplying means,
(i) determining at a determining means the amount of feed in or added to the container,
(ii) calculating the amount of feed necessary to bring the total amount of feed in the container to a predetermined amount of feed, and
(iii) supplying feed to the container in the amount calculated in step (ii) using a fine feed supplying means.

Various embodiments may preferably implement the following features:

Preferably, the determining means for performing step (i) is weight-based and comprising at least one weighing station for weighing the feed, e.g., in the container, e.g. in empty, partly filled and in filled conditions. Alternatively the weighing of the feed takes place in a feed storage or when the feed is provided to a dosing head, to the coarse feed supplying means or to the fine feed supplying means.

Alternatively or additionally the determining means for performing step (i) is volume-based and comprising at least one flow meter for measuring the amount of feed supplied by the coarse feed supplying means or the fine feed supplying means. Alternatively the measuring of the feed takes place in a feed storage or when the feed is provided to a dosing head, to the coarse feed supplying means or to the fine feed supplying means.

Alternatively or additionally the determining means for performing step (i) is volume-based and comprising at least one level sensor for measuring the level of feed in a bucket. The whole content of feed in the bucket is released for filling the container, whereby the amount is known.

Instead or additionally the determining means for performing step (i) is volume-based and comprising a bucket having a predefined volume. The whole content of feed in the bucket is released for filling the container, whereby the amount is known.

Insect larvae are added to the container, preferably the insect larvae are added after performing step (iii) for the first time. Insect larvae may also be added alternatively or additionally after performing step (o), step (i) or step (ii) for the first time.

Preferably, steps (i) to (iii) are repeated periodically or in manually set intervals for refilling feed to the container during rearing the larvae. When refilling feed to the container, there might still be feed for the larvae present in the container.

The method may further comprise transporting the container to the coarse feed supplying means for performing step (o) and/or transporting the container to the determining means for performing step (i) and/or transporting and/or stacking the container to a storage means after step (iii).

Preferably, the container is transported to the determining means before step (i). For example, the container is transported from a storage means to a weighing station in order to determine also the crate weight before step (o).

Preferably, after calculating the amount of feed in step (ii), information regarding the amount is electronically and preferably automatically transmitted to the fine feed supplying means.

Preferably, the container is automatically transported to and positioned below the fine feed supplying means. More preferably this step takes place after step (o) and/or after step (i) and/or after step (ii).

Preferably, the fine feed supplying means is configured to supply feed at a rate between 10 kg/min and 400 kg/min, and/or at the predetermined total weight the ratio of the weight of the feed to the weight of the larvae is between 0 and 1.

Preferably, the coarse feed supplying means is configured to supply feed at a rate between 60 kg/min and 500 kg/min.

Preferably, during steps (o) and/or (iii), the amount of feed in the container is monitored continuously or periodically, wherein the supplying is stopped, when the predetermined (total) amount of feed is reached. Alternatively, the weight or volume of the supplied feed is monitored continuously or periodically, wherein the supplying is stopped, when the predetermined (total) amount of feed is reached.

During steps (o) and/or (iii) the amount of feed being supplied to the container may be controlled using an observation means that comprises a flow meter or a camera. If the determining means comprises a flow meter, this flow meter can be used also as an observation means. In this case, no separate or additional flow meter is necessary as observation means for controlling the amount of feed being supplied to the container.

The invention further relates to a system for supplying feed for rearing insect larvae, preferably using the method according to any one of the preceding claims, comprising a coarse feed supplying means, a determining means for determining the amount of feed added and a fine feed supplying means for supplying feed to the container.

Preferably the determining means comprises at least one weighing station for weighing the container. The weighing station may be a separate station, preferably arranged between the coarse feed supplying means and the fine feed supplying means. In another embodiment the weighing station may be arranged at the coarse feed supplying means and/or at the fine feed supplying means.

Alternatively or additionally the determining means comprises at least one flow meter for measuring the amount of feed supplied by the coarse feed supplying means and/or at the fine feed supplying means.

The coarse feed supplying means is preferably configured to supply feed at a rate between 60 kg/min and 500 kg/min. The fine feed supplying means is preferably configured to supply feed at a rate between 10 kg/min and 400 kg/min.

The system may further comprise transporting means for, preferably automatically, transporting the container between the determining means, the supplying stations and a storage means.

The system may further comprises observation means for monitoring and for controlling the container. The observation means comprises preferably a flow meter and/or a camera for controlling the supplied amount of feed.

The coarse feed supplying means and the fine feed supplying means comprise nozzles for delivering the feed, wherein preferably the diameter of the nozzles of the coarse feed supplying means have a larger diameter than the diameter of the nozzles of the fine feed supplying means.

Alternatively or additionally the nozzles comprising closing elements, wherein at least a part of the closing elements are separately controllable for closing a part of the nozzles.

The invention is further described with reference to the drawings.

In the drawings, the same reference numerals denote the same or similar elements.

Figure 1:
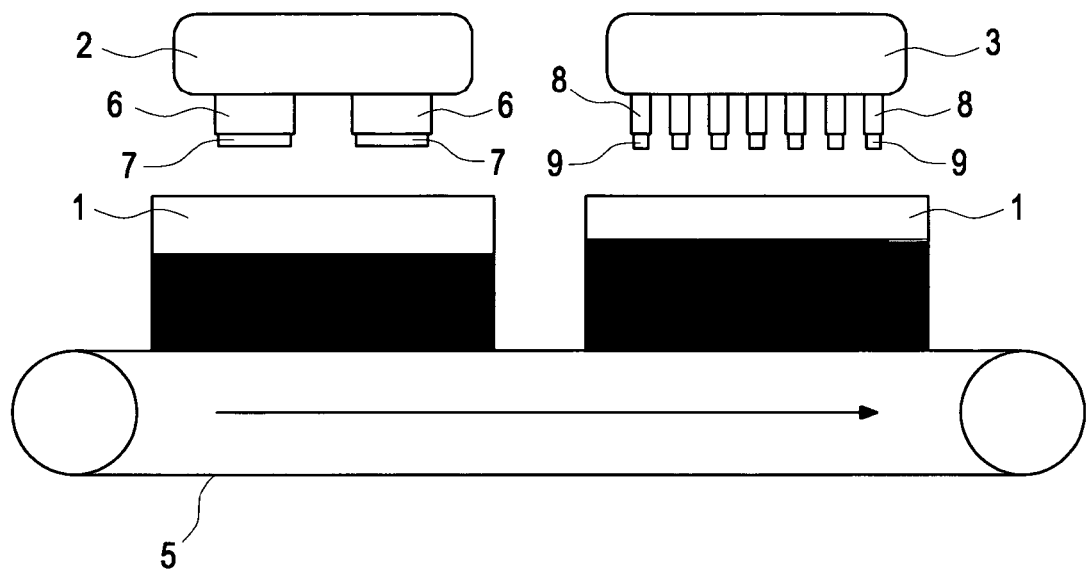
FIG. 1 shows an example according to the present invention.

FIG. 1 shows an example according to the present invention comprising a transport means 5 on which a container 1 is placed. The terms container and crate may be used interchangeably. The transport means 5 may be provided in any form such as a roller system, a conveyor belt or an autonomous robot carrying the container 1. The transport means 5 may also be manually operated. The containers 1 may be stored in a storage or rearing room in a stacked manner and may be transported to a feed supplying station automatically or manually.

The system further comprises a coarse feed supplying means 2 as well as a fine feed supplying means 3. The coarse feed supplying means 2 and the fine feed supplying means 3 may form a feed supplying station. Preferably, a liquid or flowable (wet) feed is used. The coarse feed supplying means 2 and/or the fine feed supplying means 3, 4 may comprise one or multiple nozzles 6, 8 or 10 for delivering the feed. In this case, the nozzles 6 of the coarse feed supplying means 2 may have a larger diameter than the nozzles 8 of the fine feed supplying means 3 and accordingly the fine feed supplying means 3 may comprise nozzles 8 having a smaller diameter than those of the coarse feed supplying means 2. The smaller diameter nozzles 8 of the fine feed supplying means 3 allow to more accurately control the flow of feed. In turn, the coarse feed supplying means 2 may comprise less nozzles 6 than the fine feed supplying means 3, whereas the fine feed supplying means 3 may comprise a larger number of nozzles 8 than the coarse feed supplying means 2. By providing nozzles 6, 8 or 10 it is also possible to individually provide additional feed only to certain areas of a container 1 by closing some of the nozzles 6, 8 or 10.

For closing the nozzles 6 of the coarse feed supplying means 2 closing elements 7 are provided. These closing elements 7 are separately controlled that the nozzles 6 are individual closable and thereby the amount of feed can be easily controlled or distributed area by area in the container 1. For the same reasons also the nozzles 8 or 10 of the fine feed supplying means 2 or 4 are provided with separately controllable closing elements 9 and 11. The closing elements 7, 9 and/or 10 comprises flaps, e.g. arranged by a hinge, or sliders for closing the openings of the respective nozzles 6, 8 or 10.

In case other feed than wet feed is used, other means of dosing may be suitable. The nozzles may e.g. be substituted by flaps or any other means. Furthermore, depending on the type of feed used, pumps or any other means for transport and dosing may be employed.

A camera system may additionally be provided for monitoring the content of the container 1.

Alternatively or additionally the at least one of the feed supplying means 2, 3 might be moved for supplying feed. Preferably the at least one of the feed supplying means 2, 3 is moved in direction of the container 1. A non-static feeding can be performed, whereby the processing time may be reduced.

The coarse feed supplying means 2 may be configured to quickly provide feed to a container 1. Preferably, the coarse feed filling is performed in an empty crate and corresponds more or less to about 80% of the predetermined amount of feed to be supplied. The coarse feed supply rate may be between 60 kg/min and 500 kg/min, preferably between 150 kg/min and 300 kg/min, and may exemplarily be 333 kg/min. The black part of the container 1 may indicate a filling level. After the coarse filling, the container 1 may be transported to the fine feed supplying means 3 in the direction indicated by the arrow. The fine feed supplying means 3 may then perform precise filling to a predetermined level. The amount provided by the precise filling corresponds more or less to about 20% of the predetermined amount of feed to be supplied. The feed supply rate may be between 10 kg/min and 400 kg/min, preferably between 100 kg/min and 280 kg/min and may for example be 250 kg/min. Thereby, accurate and rapid filling of feed may be achieved.

Furthermore, the system comprises a weighing station as determining means. The weighing station may for example be integrated into the transport means 5. Alternatively, each feed supplying means 2, 3 may comprise a weighing station. The weighing may be performed continuously during filling. In addition, or alternatively, the flowrate or volume of the feed may be measured by the feed supplying means 2, 3. Any suitable observation means may be employed, whereby a flow meter is preferred, arranged on or integrated in the nozzles. The filling of feed may be performed according to the measured weight and/or flow. That is, a predetermined amount of weight may be set for a container 1 and the amount of feed necessary to bring the container 1 to said predetermined amount of feed may be calculated according to the determination at the determining means, e.g., weighing station.

The containers 1 may also comprise barcodes, RFID chips or other identification means for distinguishing and identifying the containers 1. Hence, individual requirements and rearing parameters such as weight, start date of rearing, type of feed etc. may be associated to each container 1.

The observation means can comprise a camera for taking pictures of the filled containers 1. Based on an analysis of these pictures it may be defined areas inside of the container 1 which needs more additional feed than other areas of the same container 1. By controlling the nozzles 8, 10 of the fine feed supplying means 3, 4 with closing elements different amounts of feed may be added.

After initially filling feed in the container 1, involving the coarse and fine filling, insects or insect larvae of any development/growth stage may be added to the container 1. The insects may also be provided at any previous stage of the feed supply. The filling with insects may be performed at a further filling station, also manual addition of the insects might be done. The larvae of the Black Soldier Fly are often used for rearing. The weight of the larvae and of the amount of feed in one container 1 depends mainly on the size of the used container 1. E.g., for a container 1 that measures 600 mm×800 mm×290 mm, at the beginning 0.05-1.5 kg of larvae, preferably 0.2-0.85 kg of larvae, will be placed in one container 1. The amount of feed provided at the beginning for the said container may be between 15-35 kg, preferably 20-25 kg. The amount of larvae after the rearing is completed may be about 2-10 kg.

Thus, according to the numbers presented above, the ratio of larvae to feed may be between 0, at the time where only feed is present in the container, and 1, and preferably around 0.015-0.04. The container 1 may also be weighed after adding the larvae. Hence, a start weight of the filled container 1 with the larvae/feed mixture may be determined.

A rearing cycle may typically be 4-16 days, more preferably 5-8 days. By that time, the insects have reached a stage for further processing.

For rearing, the containers 1 may be stored in a rearing room, shelf, or other suitable environment with monitored climate conditions such as temperature, humidity, oxygen level, carbon dioxide level and others. The climate conditions may also provide information about the condition of the insects. The containers 1 may be automatically or manually transported to the rearing room.

In industrial scale rearing of insect larvae many parameters lead to variation in the growth of the larvae. At a certain moment in the rearing cycle of larvae, refeeding of the larvae can be required. Due to many sources of variation in the rearing process, not every rearing container requires the same amount of refeed material. This invention provides a solution to provide the desired amount of refeed to each rearing container, fully automated at a high speed.

During a rearing cycle, a container 1 may typically be refilled with feed once or twice. More than two refilling procedures may be necessary depending on the insect condition. Therefore, a feed refilling station 4 may be provided. Alternatively, the fine feed supplying means 3 or the coarse feed supplying means 2 may be used as a refilling station 4.

For refilling, a process may be used involving steps (i) to (iii) of the claimed supplying method, i.e. the method without the initial coarse feed suppling step and only involving the steps of the weighing of the container (with the feed remains and the larvae) and the accurate fine feed supplying. The container 1 may be collected from the rearing room automatically or manually and transported to the refilling station 4. There, the container is weighed and a necessary amount of feedstock is calculated. Typically, 1-10 kg of additional feed is provided during refeed. In this case, the additional feed is dosed on top of the insect/feed mixture. Residua such as livestock effluents may be removed from the container 1 if deemed necessary. The weighing may be performed before, during or after the refilling or continuously. In addition, or alternatively, a flowrate of the refilling station 4 or feed supplying means may be monitored.

In summary, the empty container 1 is first positioned below a coarse feed station 2. This station doses the largest part of the required wet feed into the container 1. A high capacity pump doses the slurry into the container 1 for a certain specified time or up to a specified weight or up to a specified volume, preferably measured volume. Then the container 1 is positioned below the fine feed station 3. Here a pump with a lower capacity doses the slurry into the container 1. This is done weight based, to obtain accurately the desired feed for each container. Thus, an optimum amount of feed may be provided at any time during a rearing cycle to ensure optimum growth of the insects.

Figure 2:
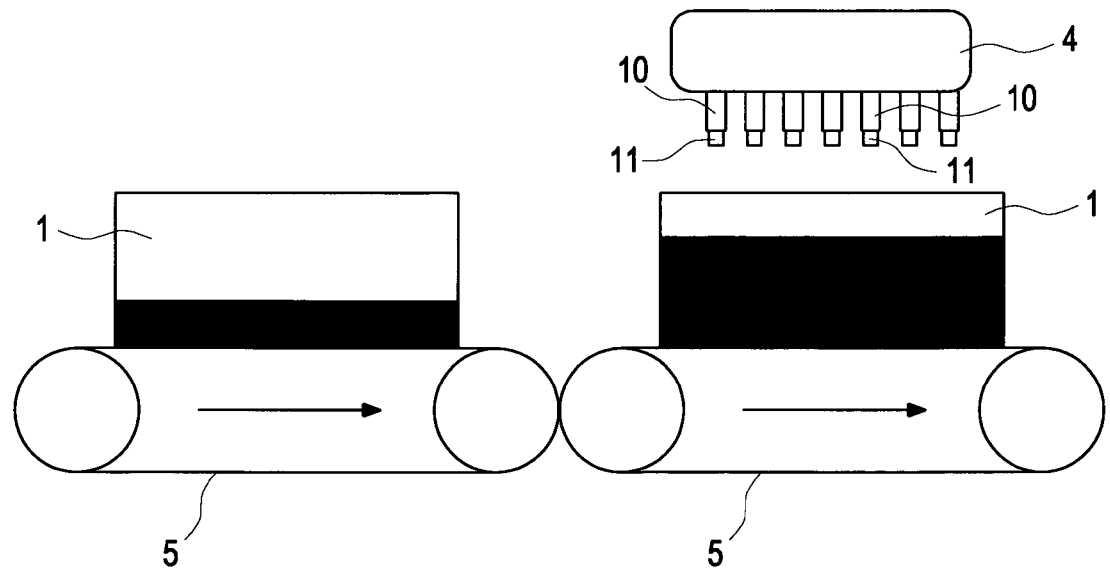
FIG. 2 shows an example according to the present invention.

FIG. 2 shows a refilling station 4 according to an example of the present invention. As noted above, the fine feed supplying means 3 of FIG. 1 and hence the complete or partial setup as described above may also be used as the refilling station 4. The nozzles 10 of the refilling station 4 comprise closure elements 11.

Therefore, the container 1 may be collected e.g. from a storage or rearing room and transported to the refilling station 4. The black part of the container 1 indicates the filling level. In FIG. 2, a two-part transport means 5 is shown. For example, different transport means may be used for transporting the containers between the different stations. Furthermore, weighing (determining) may be performed on either one of the parts, and the transport means 5 may also consist of only one part. The transport means 5 may be provided in any suitable automatic or manual form as described above.

Figure 3:
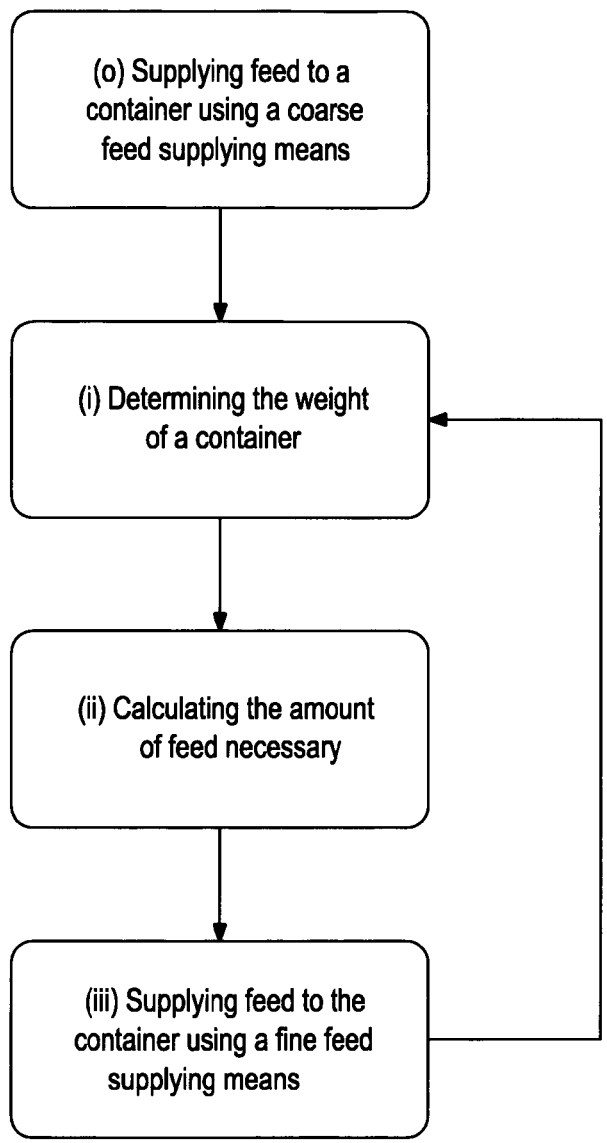
FIG. 3 shows a flowchart according to the present invention.

FIG. 3 shows a flowchart of a corresponding method. In particular, the method comprises the steps of
 (o) supplying feed to a container using a coarse feed supplying means,
 (i) determining at a determining means the amount of feed in the container,
 (ii) calculating the amount of feed necessary to bring the total amount of feed in the container to a predetermined amount of feed, and
 (iii) supplying feed to the container in the amount of feed calculated in step (ii) using a fine feed supplying means.

In step (o), a large amount of feed may initially be supplied to the container in a short period of time, preferably up to an amount less than, but close to the desired total amount of feed to be filled in the container. The amount should be sufficiently close to the desired total amount so that the following fine feed only need a reasonable period of time. However, the amount supplied during the coarse feed supplying step should not be too close to the desired total amount in order to avoid the risk of filling too much feed to the container already during the first step using the coarse feed supplying means. In practice, an amount of feed of about 65% to 95% supplied by the coarse feed supplying means and a complementary (up to totally 100%) amount of feed of about 5% to 35% supplied by the fine feed supplying means was regarded as an optimum regarding the complete required filling time.

In order to reach the desired total amount of feed as accurately as possible, the amount of feed in, e.g., the weight of, the container is then determined and the amount missing to the desired total amount of feed is determined and then supplied to the container in a controlled manner using the fine feed supplying means. For determining the missing amount, the weight of the empty container may be taken into account. This amount may then be communicated to the fine feed supplying means. The exact amount supplied during the fine feed supplying step can be controlled, for example, by continuously determining the amount of feed in the container, e.g., weighing the container during filling, using a mass flow meter and/or controlling the period of time of the fine feed supplying. Once the exact amount of feed is supplied to the container the larvae to be reared are added.

As mentioned above, it may become necessary to refill feed to the container during rearing. For doing so, a similar process may be used, with the exception that feed (and larvae) are already positioned in the container so that the step of supplying feed with the coarse feed supplying means can be omitted. That is, according to an example embodiment for refilling the container, the process may substantially comprise steps (i) to (iii) above, i.e. may comprise the following steps:
- (i) Determining the amount of feed in the container (crate) before refeed,
- (ii) Calculating desired amount of refeed, and
- (iii) Supplying the desired amount of refeed using the fine feed supplying means.

For step (iii), either the fine feed supplying means 3 already used when initially supplying feed to the container, or a dedicated fine feed supplying means 4 may be used. Also, in the latter case, however, the fine feed supplying means 4 has similar characteristics as fine feed supplying means 3.

The refeed process may additionally include the steps of communicating the desired amount of refeed to the feed station, starting dosing pump for refeed, continuous determining, e.g., weighing of the crate, and stopping dosing pump when desired amount of refeed is reached.

Manual intervention may also be possible at any time during the feed filling process.

The amount feed necessary to be refilled may depend on the actual weight of the container including the larvae and feed remains, the amount of feed and the amount of larvae initially supplied to the container. For each rearing container the desired amount of refeed is determined and dosed. In this way the existing variation between the containers is tackled and over-/underfeeding are avoided. Over-/underfeeding must be avoided to achieve maximum yield and feed conversion. The refeeding is done on a fully automated way to provide an economical process at an industrial scale. During the rearing cycle of larvae, the larvae can be refed once or multiple times to continuously have the right amount of nutrients available. This invention provides a fast and accurate way for adding the desired amount of refeed. Refeeding can be done at a speed above 200 containers per hour, preferably at a speed above 400 containers per hour. In practice, refeeding happens at a speed of 450-540 containers per hour.

In order to provide an optimum efficiency and speed of the process, the feed should show certain properties regarding consistency and composition. In order to assure the right structure of the feed mix when dosed into the larvae rearing crates, a process involving mixing of different feedstock substrates and subsequent welling of the feed mix may be applied for preparing a feed mix (feedstock).

The objective of the welling step is to assure the formation of the right structure of the final feed mix (feed) by giving the dry matter the time to soak or bind the free water and generate a puree-like feed mix but without free water for insect larvae. Thereby, optimal feed ingestions and thus optimal growth performance that highly impacts the overall productivity of the insect plant is achieved. The welling step can overcome the disadvantage of feeding the insect larvae with a feed mix of suboptimal structure which would lead to a lower feed intake and thus a lower overall productivity of the insect plant. Applying the welling step might also be helpful to minimize the dry matter content necessary to prevent free water in the final feed mix (without welling).

It is also possible to support the welling step by heating of the feed mix in order to provoke starch gelatinization and protein denaturation which would help to bind water and build the desired structure. As a side effect, this may also inactivate pathogenic microorganisms. Preferably, a welling step of the final feed mix is integrated after mixing the different feed substrates. The welling step can be performed at different locations in the process and under different conditions.

Figure 4:
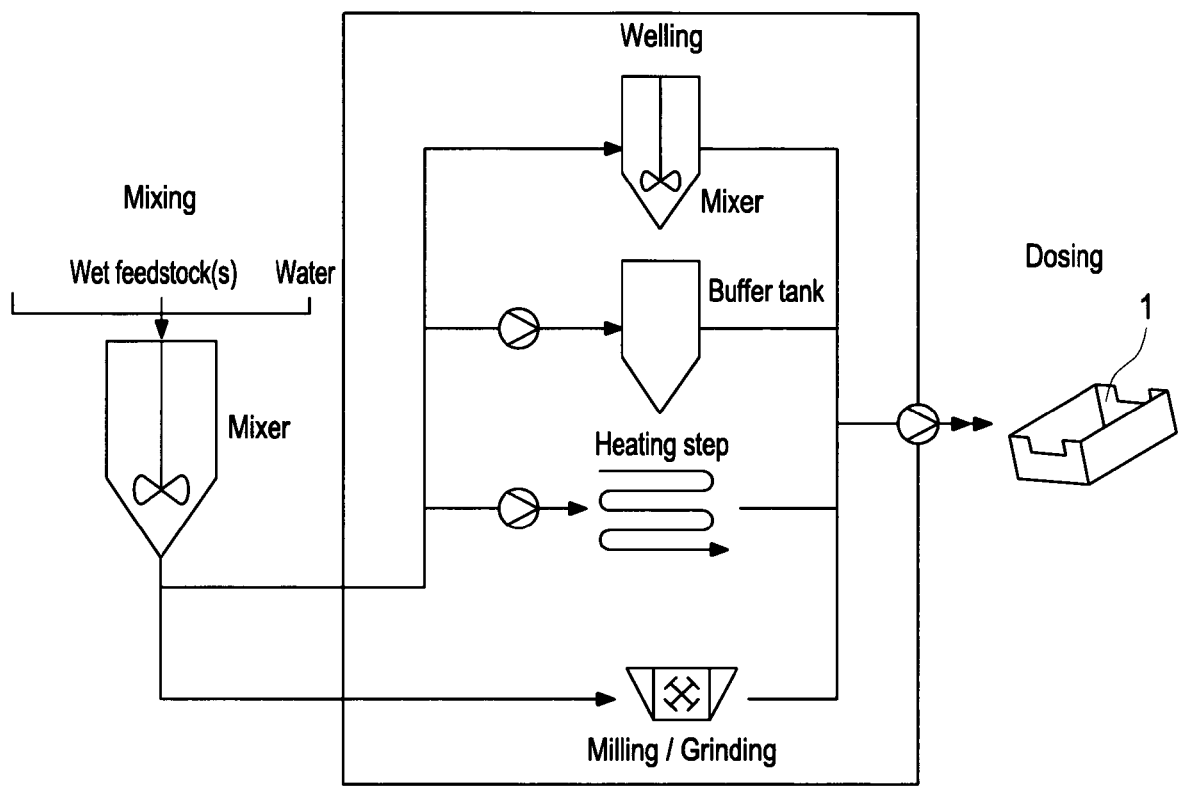
FIG. 4 shows an exemplary setup for providing a feed mix.

FIG. 4 shows an exemplary setup with different options for providing a suitable feed mix. An exemplary sequence may be as follows. At the beginning, the different feed ingredients, typically between 2-10 different feedstocks, are mixed to the final feed mix in the mixer. Preferably, the feed mix comprises between 15-40% of dry mass, typically around 30% dry mass. According to a first option, the welling time may range between 15 and 60 minutes and welling may be performed also in the mixer. The welling time in the mixer may typically be about 15 to 30 min, wherein during the welling an agitation may take place.

According to a second option, the final feed mix may be pumped from the mixer into a buffer tank and the welling may be performed in the buffer tank. The welling time may typically be 30 min and might range between 15 and 60 minutes.

In a third option, the welling step, with welling times as indicated above, may be supported by heating the final feed mix to a temperature between 50-150° C., typically about 70° C., and keeping it at the elevated temperature for the welling time.

In a fourth alternative, the welling step is supported by milling or grinding the feed mix in order to reduce the particle size and hence, the surface available for water binding.

A combination of any of the four options described may also be feasible and advantageous.

Subsequently, the feed is dosed into the rearing crates. In case of the third option, the feed mix has to be cooled down to about 25-40° C. before being dosed into the crates. The aforementioned feed mix may be used with the system and method described above.

Other aspects, features, and advantages will be apparent from the summary above, as well as from the description that follows, including the figures and the claims.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A method for supplying feed for rearing insect larvae, the method comprising the steps of:
   - (o) supplying feed to a container using a coarse feed supplying means;
   - (i) determining, by way of measures received from a container weighing station, the amount of feed that should be added to the container;
   - (ii) calculating the amount of feed necessary to bring the total amount of feed in the container to a predetermined amount of feed; and, (iii) supplying feed to the container in the amount calculated in step (ii) using a fine feed supplying means;

wherein during steps (o) and/or (iii), the amount of feed in the container is monitored continuously or periodically, wherein the supplying of feed is stopped when the predetermined amount of feed is reached.

2. The method according to claim 1, wherein the determining means for performing step (i) comprises at least one weighing station.

3. The method according to claim 2, wherein the determining means for performing step (i) also comprises at least one flow meter, the flow meter which can also be an observation means.

4. The method according to claim 1, wherein, preferably after step (iii), insect larvae are added to the container.

5. The method according to claim 1, wherein steps (i) to (iii) are repeated periodically or in manually set intervals for refilling feed to the container during rearing the larvae.

6. The method according to claim 1, further comprising transporting the container to the coarse feed supplying means for performing step (o) and/or transporting the container to the determining means for performing step (i) and/or transporting and/or stacking the container to a storage means after step (iii).

7. The method according to claim 1, wherein after calculating the amount of feed in step (ii), information regarding the amount is electronically and preferably automatically transmitted to the fine feed supplying means.

8. The method according to claim 1, wherein, preferably after step (o) and/or after step (i), the container is automatically transported to and positioned below the fine feed supplying means.

9. The method according to claim 1, wherein the fine feed supplying means is configured to supply feed at a rate between 10 kg/min and 400 kg/min and/or the coarse feed supplying means is configured to supply feed at a rate between 60 kg/min and 500 kg/min.

10. The method according to claim 1, wherein during steps (o) and/or (iii) the amount of feed being supplied to the container is controlled using observation means, said observation means comprises at least one of: a flow meter; and, a camera.

11. A system for supplying feed for rearing insect larvae, preferably using the method according to claim 1, comprising:
a coarse feed supplying means;
a fine feed supplying means; and,
at least one weighing station from which, as the determining means, to determine a ratio of feed to insect larvae weight or the weight of the container.

12. The system according to claim 11, wherein the coarse feed supplying means is configured to supply feed at a rate between 60 kg/min and 500 kg/min, and/or the fine feed supplying means is configured to supply feed at a rate between 10 kg/min and 400 kg/min.

13. The system according to claim 11, further comprising transporting means for, preferably automatically, transporting the container between the determining means for determining the container, the supplying stations and/or a storage means.

14. The system according to claim 11, further comprising an observation means for monitoring and/or for controlling the supplied amount of feed of the coarse feed supplying means and/or the fine feed supplying means, wherein the observation means comprises at least one of: a flow meter; and, a camera.

15. The system according to claim 11, wherein the coarse feed supplying means and the fine feed supplying means comprise nozzles for delivering the feed, wherein preferably the diameter of the nozzles of the coarse feed supplying means have a larger diameter than the diameter of the nozzles of the fine feed supplying means and/or the nozzles preferably comprising closing elements, wherein preferably at least a part of the closing elements are separately controllable.

16. A method for supplying feed for rearing insect larvae, the method comprising the steps of:
(o) supplying feed to a container using a coarse feed supplying means;
(i) determining a ratio of feed to insect larvae weight and, by way of measures received from a container weighing station, the amount of feed that should be added to the container;
(ii) calculating the amount of feed necessary to bring the total amount of feed in the container to a predetermined amount of feed; and,
(iii) supplying feed to the container in the amount calculated in step (ii) using a fine feed supplying means;
wherein during steps (o) and/or (iii), the amount of feed in the container is monitored continuously or periodically, wherein the supplying of feed is stopped when the predetermined amount of feed is reached.

17. The method according to claim 16, wherein the determining means for performing step (i) comprises at least one weighing station.

18. The method according to claim 16, wherein, preferably after step (iii), insect larvae are added to the container.

19. The method according to claim 16, wherein steps (i) to (iii) are repeated periodically or in manually set intervals for refilling feed to the container during rearing the larvae.

* * * * *